United States Patent [19]

Hintze

[11] Patent Number: 4,749,686

[45] Date of Patent: Jun. 7, 1988

[54] COMBINATIONS OF RENAL VASODILATORS AND $\alpha_1$-ADRENERGIC OR GANGLIONIC BLOCKING AGENTS AND METHODS FOR TREATING DISEASES

[75] Inventor: Thomas H. Hintze, Montrose, N.Y.

[73] Assignee: New York Medical College, Valhalla, N.Y.

[21] Appl. No.: 937,903

[22] Filed: Dec. 4, 1986

[51] Int. Cl.⁴ .............................................. A61K 37/02
[52] U.S. Cl. ........................................................ 514/12
[58] Field of Search ............................................ 514/12

[56] References Cited

PUBLICATIONS

Chem. Abstr. vol. 71, (1969) 69158.
Chem. Abstr. vol. 103 (1985) 64636.
Chem. Abstr. vol. 106 (1987) 60959.
Chem. Abstr. vol. 105 (1986) 209252.
Chem. Abstr. vol. 104, (1986) 82397.
Chem. Abstr. vol. 103 (1985) 87727.
Chem. Abstr. vol. 99, (1983) 191046.

*Primary Examiner*—Delbert R. Phillips
*Attorney, Agent, or Firm*—Patricia A. Martone

[57] ABSTRACT

This invention relates to combinations and methods for the treatment of renal disease, cardiovascular disease and hypertension. More particularly, the invention relates to combinations of renal vasodilators and $\alpha_1$-adrenergic or ganglionic blocking agents. According to a preferred embodiment, atriopeptins having renal vasodilator activity are used in combination with $\alpha_1$-adrenergic blocking agents for treating renal disease, cardiovascular disease and hypertension. The blocking agent promotes sustained renal vasodilation, thereby enhancing renal blood flow and kidney function.

20 Claims, 6 Drawing Sheets

| | Control | Change From Control | | |
|---|---|---|---|---|
| | | 5 min | 40 min | 60 min |
| Mean Arterial Pressure (mmHg) | | | | |
| unblocked | 97±7.7 | -15±1.7* | -10±2.4* | -10±3.6* |
| $\alpha_1$ blockade | 88±5.4 | -10±0.5* | -7.5±0.9* | -9.0±1.3* |
| Mean Renal Blood Flow (ml/min) | | | | |
| unblocked | 270±33 | 33±3.0* | -21±10* | -15±11* |
| $\alpha_1$ blockade | 275±9.6 | 42±2.7* | 37±4.4* | 38±6.9* |
| Renal Vascular Resistance (mmHg) | | | | |
| unblocked (ml/min) | 0.39±.09 | -0.11±.03* | -.04±.03 | -.03±.03 |
| $\alpha_1$ blockade | 0.32±.03 | -0.11±.01* | -.06±.01 | -.07±.01* |
| Heart Rate (b/min) | | | | |
| unblocked | 80±2.8 | 5.0±6.6 | 8.0±3.7 | 3.0±4.0 |
| $\alpha_1$ blockade | 87±4.4 | 16±4.0* | 13±3.9* | 12±2.7* |
| Urine Flow Rate (ml/min) | | | | |
| unblocked | 0.53±.02 | .54±.09* | .52±.03* | .51±.09* |
| $\alpha_1$ blockade | 0.65±.10 | .43±.14* | .61±.17 | .58±.09* |
| GFR (ml/min) | | | | |
| unblocked | 72±14 | 82±7.7* | 79±13* | 57±14* |
| $\alpha_1$ blockade | 41±11 | 26±8.0*† | 36±7.4*† | 44±13* |
| Sodium Excretion (µeq/min) | | | | |
| unblocked | 106±65 | 129±19* | 152±17* | 147±31* |
| $\alpha_1$ blockade | 84±13 | 73±11*† | 123±39* | 122±22* |
| Potassium Excretion (µeq/min) | | | | |
| unblocked | 64±12 | 74±12* | 68±10* | 66±5.1* |
| $\alpha_1$ blockade | 73±12 | 42±15* | 45±23* | 52±11* |
| Hematocrit (%) | | | | |
| unblocked | 41±0.8 | 0.5±0.3 | 1.0±0.4* | 1.0±0.4* |
| $\alpha_1$ blockade | 42±0.9 | -0.5±0.3 | 0.8±0.3* | 0.8±0.3 |

(* $p<0.05$ from control, † $p<0.05$ from unblocked)
plasma K= 3.75±13 µeq/l and did not change
plasma Na= 145±1.5 µeq/l and did not change

| | Control | 15 min | 35 min | 55 min | 85 min | 115 min |
|---|---|---|---|---|---|---|
| URINE FLOW RATE (ml/min) | 0.04±.01 | 1.0±.02* | 0.8±0.1* | 0.8±0.1* | 0.6±0.2* | 0.5±0.2* |
| GFR (ml/min) | 2.55±.37 | 15.9±2.2* | 13.9±2.3* | 13.0±0.8* | 12.9±0.6* | 9.4±0.9* |
| SODIUM EXCRETION (µeq/min) | .39±.03 | 66±7.9* | 85±23* | 64±7.4* | 78±16* | 62±20* |
| POTASSIUM EXCRETION (µeq/min) | 1.9±0.4 | 14±5.1* | 10±3.8* | 6.8±2.2* | 11±1.9* | 9.0±1.4* |
| PLASMA SODIUM (meq/l) | 146±0.7 | 146±1.0 | ---- | 147±1.3 | ---- | 146±1.9 |
| PLASMA POTASSIUM (meq/l) | 3.5±0.1 | 3.4±0.1 | ---- | 3.5±0.2 | ---- | 3.4±0.1 |
| HEMATOCRIT % | 32±0.6 | 30±0.1 | ---- | 31±2.0 | ---- | 34±2.2 |
| MEAN ARTERIAL PRESSURE (mmHg) | 101±12 | 86±8.2* | 76±8.4* | 75±6.2* | 71±5.9* | 74±6.5* |
| HEART RATE (b/min) | 161±14 | 164±13 | 163±12 | 163±12 | 161±12 | 161±12 |

(n=5, data are values attained prior to and during the infusion of atriopeptin 24; * $p<0.05$ from control)

COMBINATIONS OF RENAL VASODILATORS AND α₁-ADRENERGIC OR GANGLIONIC BLOCKING AGENTS AND METHODS FOR TREATING DISEASES

TECHNICAL FIELD OF INVENTION

This invention relates to combinations and methods for the treatment of renal disease, cardiovascular disease and hypertension. More particularly, this invention relates to combinations of renal vasodilators and $\alpha_1$-adrenergic or ganglionic blocking agents, the combinations being useful for the promotion of sustained renal vasodilation in the above-identified disease states. According to a preferred embodiment of the invention, the combination comprises an atriopeptin having renal vasodilator activity and an $\alpha_1$-adrenergic blocking agent. The $\alpha_1$-adrenergic blocking agent sustains the renal vasodilator effect of the atriopeptin, thereby enhancing renal blood flow and kidney function in the treatment of renal disease, cardiovascular disease and hypertension.

BACKGROUND OF THE INVENTION

Atriopeptins are polypeptides isolated from mammalian atria that display diuretic and natriuretic activity. These atrial polypeptides have been purified and sequenced [see, e.g., U.S. Pat. No. 4,496,544 issued to P. Needleman; M. G. Currie et al., "Purification And Sequence Analysis Of Bioactive Atrial Peptides (Atriopeptins)", *Science*, 223, pp. 67-69 (1984); T. G. Flynn et al., "The Amino Acid Sequence Of An Atrial Peptide With Potent Diuretic And Natriuretic Properties", *Biochem. Biophys. Res. Comm.*, 117 (No. 3), pp. 859-65 (1983)]. These peptides have also been referred to in the art as cardionatrin [see, e.g., A. J. deBold et al., "Cardionatrin I - A Novel Heart Peptide With Potent Diuretic And Natriuretic Properties", *Life Sci.*, 33, pp. 297-302 (1983)] and atrial natriuretic factors or peptides [see, e.g., N. G. Seidah et al., "Amino Acid Sequence Of Homologous Rat Atrial Peptides", *Proc. Natl. Acad. Sci. USA*, 81, pp. 2640-44 (1984) and K. Kangawa et al., "Purification And Complete Amino Acid Sequence Of Beta-Rat Atrial Natriuretic Polypeptide ($\beta$-rANP) Of 5,000 Daltons", *Biochem. Biophys. Res. Comm.*, 119 (No. 3), pp. 933-40 (1984)].

While all atriopeptins appear to possess diuretic and natriuretic activity, the atriopeptins have been further characterized as comprising several subtypes that display different muscle relaxant activities. Atriopeptin 21 (also referred to in the art as atriopeptin I) is a 21-amino acid polypeptide that relaxes only intestinal smooth muscle in vitro. Atriopeptins 23 and 24 (also known in the art as atriopeptins II and III, respectively) have the same amino acid sequence as atriopeptin 21 except for an additional Phe-Arg or Phe-Arg-Tyr, respectively, at the carboxy terminal end of the peptide. These atriopeptins relax both intestinal and vascular smooth muscles in vitro [see, e.g., M. G. Currie et al., supra; R. J. Winquist et al., "Atrial Natriuretic Factor Elicits An Endothelium Independent Relaxation And Activates Particulate Guanylate Cyclase In Vascular Smooth Muscle", *Proc. Natl. Acad. Sci.*, 81, pp. 7661-64 (1984)]. Furthermore, atriopeptins 23 and 24 have been shown to selectively increase renal blood flow and decrease renal vascular resistance [see, e.g., T. Oshima et al., "An Atrial Peptide Is a Potent Renal Vasodilator Substance", *Circ. Res.*, 54, pp. 612-16 (1984)].

Thus, it is known that atriopeptins 23 and 24 are potent selective renal vasodilators that affect the renal vascular bed in a dosage-dependent fashion. Although the catecholamine, dopamine, is also known to possess renal vasodilator effects, dopamine reduces the resistance in other vascular beds as well and therefore does not display the unique renal specificity exhibited by the atriopeptins. [See, e.g., T. H. Hintze et al., "Atriopeptins: Renal-Specific Vasodilators In Conscious Dogs", *Am. J. Physiol.*, 248, pp. H587-91 (1985)]. Studies to date, however, have indicated that the renal vasodilator activity of atriopeptins 23 and 24 is transient [see T. H. Hintze et al., supra].

It is known that norepinephrine, epinephrine and other sympathomimetic amines or catecholamines act at various target sites within the body to mediate the wide range of central and peripheral functions of the sympathetic nervous system. Those sites are characterized by the presence of one or both of two distinct receptors specific for catecholamines. These receptors have been designated the $\alpha$- and $\beta$-adrenergic receptors and have been further characterized into subclasses. For example, $\beta_1$-adrenergic receptors are found primarily in cardiac tissue, $\beta_2$-adrenergic receptors are found in smooth muscle tissue and gland cells, $\alpha_1$-adrenergic receptors are found primarily at postsynaptic effector sites in smooth muscle tissue and gland cells and $\alpha_2$ receptors are found on nerve terminals. Thus, the catecholamines exert their homeostatic regulatory activity via an initial binding to these receptors on the surface of the cells of the particular tissue to be regulated. Furthermore, it is well established that the catecholamines exert different, often contrasting effects, on the tissues of the body depending upon whether they bind to an $\alpha$- or $\beta$-receptor. For a general review of the sympathetic nervous system, in particular, the biology and mechanisms of action of the catecholamines, see A. G. Gilman et al. (eds.), *The Pharmacological Basis Of Therapeutics*, Chapter 8, pp. 138-75, MacMillan Publishing Co., Inc., New York (6th ed. 1980).

It is also known that certain chemical compounds interfere with the ability of the catecholamines to bind to their target $\alpha$- or $\beta$-receptors. These compounds have been termed adrenergic receptor blocking agents, more specifically, $\alpha$- or $\beta$-adrenergic antagonists. These agents act by binding selectively to either the $\alpha$ or $\beta$ class of adrenergic receptor, thus preventing the catecholamine from binding to the receptor and exerting its effect.

The $\alpha$- and $\beta$-adrenergic blocking agents are two distinct classes of compounds with different biological effects and uses. This is so because they are compounds that interact with different receptor molecules on different tissues and interfere with different catecholamine effects. For example, since the effect of catecholamine interaction with $\alpha_1$-receptors in smooth muscle is generally excitatory, an $\alpha_1$-adrenergic blocking agent, such as prazosin, causes a relaxation or dilation of the muscle tissue. In contrast, since the effect of catecholamine action on $\beta_2$-receptors in smooth muscle is inhibitory, $\beta_2$-adrenergic blocking agents generally cause a constriction of that tissue. Furthermore, because the effects of the catecholamines vary depending upon the tissue on which they are acting, the amounts and types of receptors in that tissue and the particular catecholamine in question, the action and use of any particular adrenergic blocking agent will depend upon these factors as well. For a general review of these blocking agents and their varying effects, see A. G. Gilman et al. (eds.), *The Pharmacological Basis Of Therapeutics,* supra, pp. 176–210.

Alternatively, ganglionic blocking agents act at the autonomic ganglia of the sympathetic nervous system and cause a decrease in the release of the catecholamine, norepinephrine, thereby eliminating stimulation of $\alpha$ receptors in the various tissues of the body. In this way, these agents indirectly block the interaction of norepinephrine with $\alpha$ receptors.

The general use of $\beta$-adrenergic blocking agents in the treatment of hypertension and cardiovascular disease is known. For example, the use of a $\beta$-adrenergic blocking agent in combination with a vasodilator and a diuretic for the treatment of arterial hypertension was referred to in German patent application No. 2230010. Similarly, U.S. Pat. No. 4,529,604, issued to C. Kaiser, refers to the use of the well known $\beta$-blocking agent, propranolol, in combination with dopamine derivatives, to potentiate the vasodilator effect of the dopamine compounds for the treatment of hypertension. Compounds possessing both $\beta$-adrenergic blocking and vasodilator activities for the treatment of hypertension were referred to in U.S. Pat. Nos. 4,053,605, 4,092,419 and 4,139,535, issued to J. J. Baldwin, U.S. Pat. No. 4,495,352, issued to W. E. Kreighbaum, and Japanese patent application No. 0044678 and 0225069. And, European patent application 106,335.7 refers to pharmaceutical compositions which may include a $\beta$-adrenergic blocking agent together with a coronary vasodilator for the treatment of coronary heart disease.

The potential of $\alpha$-adrenergic and ganglionic blocking agents for therapeutic uses is less established. This is due to the possibility of several side effects of treatment at high dosage such as postural hypotension [see, e.g., U.S. Pat. No. 4,001,238, issued to R. A. Partyka and A. G. Gilman et al. (eds.), *The Pharmacological Basis Of Thereaputics,* supra, pp. 186–88 and 211–19].

DISCLOSURE OF THE INVENTION

The present invention relates to combinations and methods for the treatment of renal disease, cardiovascular disease and hypertension. More particularly, the invention relates to combinations comprising renal vasodilators and $\alpha_1$-adrenergic or ganglionic blocking agents. According to a preferred embodiment of this invention, atriopeptins having renal vasodilator activity are used in combination with $\alpha_1$-adrenergic blocking agents for treating the above-identified diseases. Advantageously, the combinations and methods of this invention promote sustained renal vasodilation, thus enhancing renal blood flow and kidney function in the treatment of those diseases.

BRIEF DESCRIPTION OF THE DRAWINGS

FIG. 3 depicts in table form the effects in conscious dogs of a one-hour infusion of atriopeptin 24 (5 $\mu$g/kg/min) on renal hemodynamics and function before and after $\alpha_1$-adrenergic receptor blockade.

In FIGS. 1, 3, 4, 5, and 6, the asterisks represent a statistically significant change ($p < 0.05$) from their respective control values.

BEST MODE OF CARRYING OUT THE INVENTION

In order that the invention herein described may be more fully understood, the following detailed description is set forth.

In the description, the following terms are employed:

Atriopeptins—Polypeptides isolated from mammalian atria that possess diuretic and natriuretic activities. A number of these atrial polypeptides are also renal-specific vasodilators which cause a marked increase in renal blood flow and a marked decrease in renal vascular resistance.

$\alpha_1$-Adrenergic Blocking Agents—Compounds that bind to the $\alpha_1$ subclass of adrenergic receptors, thus inhibiting the ability of catecholamines, such as epinephrine and norepinephrine, from interacting effectively with those receptors. These blocking agents include compounds that bind solely to the $\alpha_1$-receptor as well as compounds that bind to the $\alpha_1$-receptor and the other $\alpha$-receptor subclasses.

Ganglionic Blocking Agents—Compounds that block transmission of nerve impulses in autonomic ganglia by either preventing depolarization of the ganglia or by blocking nicotinic receptors on the ganglia. Either mechanism of action causes a decrease in the release of norepinephrine from the post ganglionic neuron.

Renal Disease—Any disease characterized by a dysfunction of the kidney.

Cardiovascular Disease—Any disease characterized by a dysfunction of the heart and blood vessels.

Hypertension—A systemic condition characterized by abnormally high blood pressure or peripheral vascular resistance.

The present invention relates to combinations and methods for treating renal disease, cardiovascular disease and hypertension. More particularly, this invention relates to combinations of pharmaceutically effective amounts of a renal vasodilator and pharmaceutically effective amounts of a compound selected from the group consisting of $\alpha_1$-adrenergic blocking agents and ganglionic blocking agents. These blocking agents prolong the effects of the renal vasodilator. The combinations of this invention, therefore, result in a sustained renal vasodilation which promotes increased renal blood flow and kidney function.

The present invention also relates to methods for treating renal disease, cardiovascular disease and hypertension comprising the step of treating a mammal in a pharmaceutically acceptable manner with a pharmaceutically effective amount of a renal vasodilator and a pharmaceutically effective amount of a compound selected from the group consisting of $\alpha_1$-adrenergic blocking agents and ganglionic blocking agents.

Without being bound by theory, I believe that the effectiveness of the combinations and methods of this invention over the use of renal vasodilators alone is due to the action of the $\alpha_1$-adrenergic or ganglionic blocking agents in blocking an adrenergic renal vasoconstriction that follows renal vasodilation. It is believed that the reduction in arterial pressure caused by the administration of the vasodilator unloads the systemic arterial baroreflexes resulting in an adrenergic renal vasoconstriction as well as tachycardia and positive inotropic action. In laboratory experiments, these effects were eliminated by adrenergic receptor blockade. Thus, the adrenergic renal vasoconstriction following the administration of a renal vasodilator may represent the renal efferent arm of this reflex. The, the blocking agents of this invention may prevent this reflex renal vasoconstriction. Accordingly, the use of a renal vasodilator in combination with an $\alpha_1$-adrenergic or ganglionic blocking agent results in a sustained renal vasodilation, thereby allowing increased renal blood flow and enhanced kidney function.

The combinations and methods of this invention are useful in the treatment of renal disease in that they promote renal vasodilation and increase the glomerular filtration rate (GFR) and sodium excretion. Additionally, these combinations and methods are useful for the treatment of cardiovascular disease and hypertension in that they cause a suppression of the renin-angiotensin-aldosterone system. This suppression promotes vasodilation of blood vessels in the body and increases the excretion of sodium and water by the renal tubules, resulting in a decrease in blood pressure.

According to a preferred embodiment, the renal vasodilator is an atriopeptin having renal vasodilator activity. Atriopeptins are advantageously used in the combinations and methods of the invention because they possess diuretic and natriuretic activities, in addition to their renal vasodilator effects. Thus, they further promote kidney function as well as increase renal blood flow in the treatment of renal disease, cardiovascular disease and hypertension.

The use of these preferred combinations and methods advantageously produced a sustained renal vasodilation in conscious dogs that was not seen upon administration of an atriopeptin alone. According to experimental data, when atriopeptin 24 was administered alone, there was a marked increase in renal blood flow and a marked decrease in renal vascular resistance and arterial pressure. However, this renal vasodilation was transient, lasting only approximately 10 minutes during a one-hour infusion of atriopeptin 24. When an $\alpha_1$-adrenergic blocking agent such as prazosin was administered 40 minutes before the atriopeptin 24 infusion, the renal blood flow remained elevated for the duration of the atriopeptin 24 infusion (see Example 1, infra).

The atriopeptins useful in the combinations and treatments of this invention are those atriopeptins that exhibit selective renal vasodilator activity. For example, these atriopeptins include atriopeptin 23, atriopeptin 24 and atriopeptin 28, the circulating form of the atriopeptins [see D. Schwartz et al., "Ser-leu-arg-arg-atriopeptin III: The Major Circulating Form Of Atrial Peptide", *Science*, 229, pp. 397–400 (1985)].

These natural atriopeptins have been purified and characterized [see, for example, U.S. Pat. No. 4,496,544, issued to P. Needleman; A. J. deBold, supra; and M. G. Currie et al., supra]. Atriopeptins useful in the combinations and treatments of this invention may also be produced and purified in large amounts using recombinant DNA technology [see, e.g., PCT patent application No. WO 85/04870; M. Maki et al., "Cloning Of Genomic DNA For Human Atrial Natriuretic Factor", *Biochem. Biophys. Res. Comm.*, 125 (No. 2), pp. 797–802 (1984); and C. E. Seidman et al., "The Structure Of Rat Preproatrial Natriuretic Factor As Defined By A Complementary DNA Clone", *Science*, 225, pp. 324–26 (1984)]. The atriopeptins may also be synthesized chemically [see, e.g., M. G. Currie et al., supra, p. 69]. Other renal vasodilators useful in the combinations and methods of this invention include, but are not limited to, dopamine and its derivatives.

The $\alpha_1$-adrenergic blocking agents useful in the combinations and methods of this invention are those compounds which bind to the $\alpha_1$ subclass of adrenergic receptors and thereby block the ability of catecholamines from interacting effectively with those receptors. It is to be understood that these compounds include those that bind only to the $\alpha_1$ subclass of receptors as well as compounds that bind to the $\alpha_1$ receptor and the other $\alpha$ receptors. Thus, any compound that binds at least to an $\alpha_1$ receptor falls within the scope of the present invention. These compounds include, but are not limited to, prazosin and its derivatives, such as trimazosin, the haloalkylamines such as phenoxybenzamine and dibenomine, phentolamine, tolazoline, azapetine, chlorpromazine, haloperidol, the benzodioxans, and the ergot alkaloids.

Furthermore, an alternative embodiment of the invention comprises the use of a ganglionic blocking agent such as hexamethonium, in combination with a renal vasodilator such as an atriopeptin. The ganglionic blocking agent acts at the autonomic ganglia to eliminate stimulation of the $\alpha_1$-adrenergic receptors in the kidney and other tissues containing those receptors. The ganglionic blocking agent therefore merely acts at an earlier point along the sympathetic pathway to block stimulation of the $\alpha_1$ receptor. Other ganglionic blocking agents to be used in the combinations and methods of this invention include, but are not limited to pentolinium, chlorisondamine, trimethidinium, trimethaphan, mecamylamine, and pempidine.

The combinations and methods of this invention are useful in treating any mammal, including humans. Renal vasodilators derived from the target patient species are preferably used. However, renal vasodilators derived from other species may be used in the combinations and methods of this invention if they are active in the target cells. For example, rat-derived atriopeptins have been shown to be active on rabbit and chick tissue in vitro [see, e.g., U.S. Pat. No. 4,496,544 columns 9–10].

According to a preferred embodiment of the invention, mammals are treated with pharmaceutically effective amounts of two active components—an atriopeptin having renal vasodilator activity and an $\alpha_1$-adrenergic blocking agent. These two components can be administered simultaneously or sequentially, the $\alpha_1$-adrenergic blocking agent being given before or after atriopeptin treatment. According to a preferred embodiment, the $\alpha_1$-adrenergic blocking agent is administered prior to the administration of the atriopeptin. This sequential administration involves treatment with the $\alpha_1$-adrenergic blocking agent at least within 24 hours and preferably, within one to two hours, prior to treatment with the atriopeptin and may involve periodic subsequent treatments with the blocking agent. The atriopeptin and $\alpha_1$-blocking agent may be administered to the patient at one time or over a series of treatments.

The renal vasodilators and $\alpha_1$-blocking agents of the invention can be administered using conventional modes of administration including, but not limited to, oral, parenteral, subcutaneous or intravenous administration. Intravenous administration may be by injection or infusion. According to a preferred embodiment, the atriopeptin is administered by intravenous infusion and the $\alpha_1$ blocking agent is administered orally. An osmotic pump may be implanted under the skin for continuous administration of the atriopeptin.

The compositions of the invention—comprising the renal vasodilator or blocking agent alone or in combination—may also be in a variety of forms. These include, for example, solid, semi-solid and liquid dosage forms, such as tablets, pills, powders, liquid solutions or suspensions, polymeric microcapsules or microvesicles, liposomes or capsules comprising diazo-compounds, suppositories, and injectable or infusable solutions. The preferred form depends on the intended mode of administration and therapeutic application. For example, according to a preferred embodiment of the invention wherein the renal vasodilator is an atriopeptin, oral administration of the atriopeptin is disfavored and intravenous administration is preferred. This is due to the fact that the atriopeptin protein tends to be degraded in the stomach when taken orally, e.g., in tablet or powder form.

The compositions of the invention also preferably include conventional pharmaceutically acceptable carriers and adjuvants which are known to those of skill in the art, such as ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol.

The most effective mode of administration and dosage regimen of the renal vasodilator and $\alpha_1$-adrenergic or ganglionic blocking agent will depend upon the type of disease to be treated, the severity and course of that disease, previous therapy, the patient's health and response to the treatment and the judgment of the treating physician. Thus, dosages of the renal vasodilator and $\alpha_1$-adrenergic or ganglionic blocking agent may be titrated to the individual patient.

However, an effective dose of the renal vasodilator, such as the atriopeptin of the preferred embodiment, may be in the range of from about 0.1 $\mu$g/kg to about 100 $\mu$g/kg. More preferably, the effective dose of the atriopeptin is from about 0.1 $\mu$g/kg to about 10 $\mu$g/kg. An effective dose of the $\alpha_1$-adrenergic blocking agent, such as prazosin, may be in the range of from about 0.1 mg/kg to about 1 mg/kg by mouth. And, an effective dose of the ganglionic blocking agent may be in the range of from about 0.1 mg/kg to about 10 mg/kg by mouth. Within these dosage ranges, any side effects of the $\alpha_1$-adrenergic or ganglionic blocking agent are negligible.

The preferred compositions of the invention include compositions comprising an atriopeptin or $\alpha_1$-adrenergic blocking agent alone or a composition comprising a combination of the two components to be used when simultaneous administration is desired.

In order that the invention described herein may be more fully understood, the following example is set forth. It should be understood that this example is for illustrative purposes only, and is not to be construed as limiting this invention in any manner.

EXAMPLE 1

This example demonstrates the in vivo effect of treatment with an $\alpha_1$-adrenergic blocking agent on the vasodilation produced by the administration of atriopeptin 24. In this example, I first infused conscious dogs for one hour with atriopeptin 24 and measured the effects on renal hemodynamics and function. At least one week later, I treated the same dogs with the $\alpha_1$-adrenergic blocking agent, prazosin, 40 minutes prior to a one-hour atriopeptin 24 infusion. The data set forth below demonstrate the transient renal vasodilation seen when atriopeptin 24 is administered alone and the sustained renal vasodilation that is achieved when an $\alpha_1$-adrenergic blocking agent is administered prior to atriopeptin treatment.

The experiments were conducted using the following techniques and devices: female mongrel dogs were instrumented using sterile surgical techniques under sodium pentobarbital anesthesia (25 mg/kg). To measure renal blood flow, a Doppler ultrasonic flow transducer (Parks Electronics) was placed around the left renal artery. To measure arterial pressure, a Tygon catheter was positioned in the abdominal aorta. These surgical procedures were accomplished through a midline laparotomy. The animals were allowed 10 days to two weeks to recover before experiments were begun. During this period, the dogs became accustomed to the placement of a urinary bladder catheter (Foley, 12) for urine collection.

Arterial pressure was recorded using the implanted catheter attached to a Statham P23Db strain gauge transducer. Renal blood flow was measured using an ultrasonic flowmeter (Model 806A, Parks Electronics) and the implanted Doppler flow transducer. Phasic arterial pressure and renal blood flow were recorded on magnetic tape (Bell and Howell 3700B) and played back on a direct writing oscillograph (Gould-Brush 2800S). Mean flow and pressure were derived using 2 Hz filters. Heart rate was calculated using a cardiotachometer (Beckman Model 80574) from the pressure pulse interval. All of these techniques have been previously described [see T. H. Hintze and S. F. Vatner, "Cardiac Dynamics During Hemorrhage: Relative Unimportance Of Adrenergic Inotropic Responses", *Circ. Res.*, 50, pp. 705–13 (1982); T. H. Hintze and S. F. Vatner, "Reactive Dilation Of Large Coronary Arteries In Conscious Dogs", *Circ. Res.*, 54, pp. 50–57 (1984); T. H. Hintze et al., "Atriopeptins: Renal-Specific Vasodilators In Conscious Dogs", *Am. J. Physiol.*, 248, pp. H587–91 (1985); and T. H. Hintze et al., "Apparent Reduction In Baroreflex Sensitivity To Adenosine In Conscious Dogs", *Am. J. Physiol.*, 249, pp. H554–59 (1985)].

To measure renal function, urine samples were taken from the dogs, urine volume was measured and the concentration of urine and plasma sodium (Na) and potassium (K) was assayed using a flame photometer (Instrumentation Laboratories, Model 343). Urine flow rate was calculated knowing the volume of urine collected and the collection interval. To measure the glomerular filtration rate, a loading dose of inulin (3 ml/kg) (American Critical Care) was administered one hour prior to atriopeptin administration and an infusion (2 ml/kg/hr) begun which lasted for the entire period of the experiment. Plasma and urine samples were taken simultaneously for the analysis of inulin concentration using a spectrophotometric assay [D. L. Maude and G. Kao-Lo, "Salt Excretion And Vascular Resistance Of Perfused Kidneys Of Dahl Rats", *Hypertension*, 4, pp. 532–37 (1982)]. Hematocrit was also measured in each blood sample.

All data were stored on a Digital computer (Dec Pro 350). Renal vascular resistance was calculated as the quotient of mean arterial pressure and renal blood flow. Mean and standard errors of the mean were calculated for each collection period. A one-way analysis of variance was used to determine changes which were significantly different from control. A two-way analysis of variance was used to determine differences between atriopeptin 24 before and after $\alpha_1$-adrenergic receptor blockade [G. W. Snedecor and W. G. Cochran, *Statistical Methods*, Iowa State University Press, pp. 258–334 (Ames, Iowa, 1978)].

The experiments were conducted as follows: atriopeptin 24 was infused into five dogs for one hour at a rate of 5 $\mu$g/kg/min and changes in renal hemodynamics and function were measured.

Urine was collected at two 20-min periods prior to atriopeptin administration and every 10 min during the one-hour atriopeptin infusion. Recordings of phasic and mean arterial pressure and renal blood flow and heart rate were made for at least 10 min prior to the infusion of the atriopeptin and prior to each urine collection during the one-hour infusion. During the infusion, data were taken for measurement of glomerular flow rate, Na, and K every 10 min.

Figure 1:
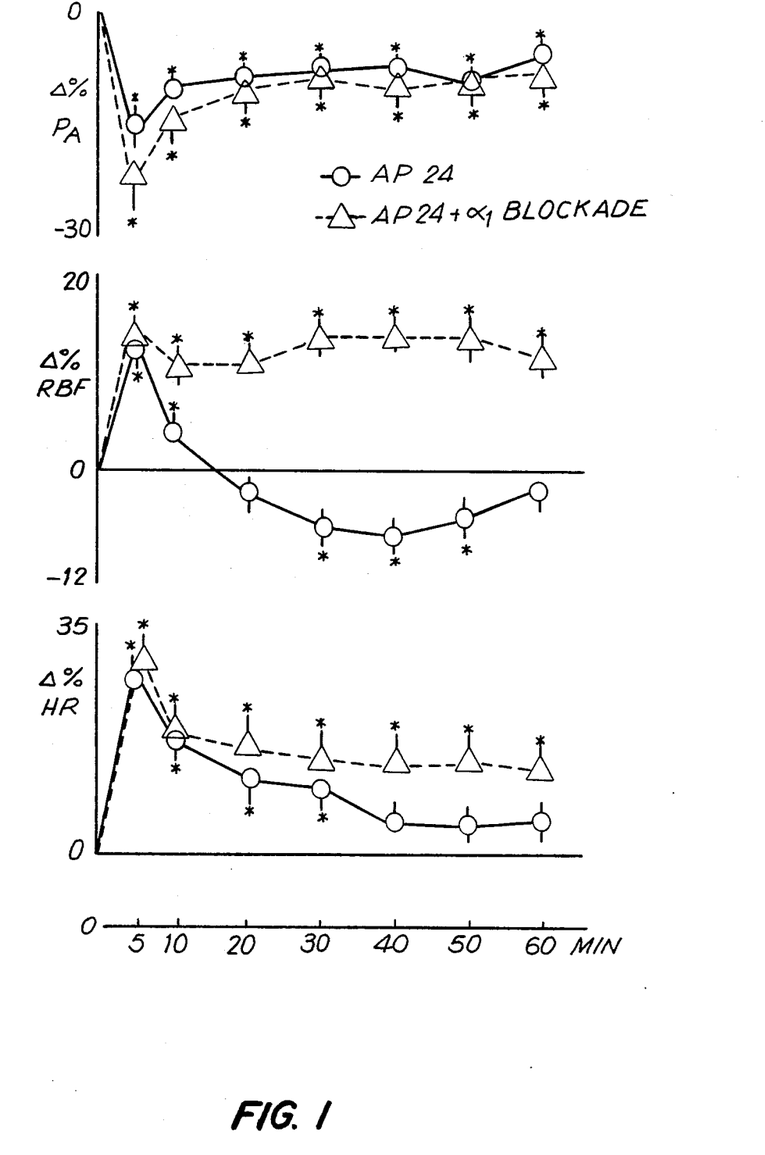
FIG. 1 depicts in graph form the effects on arterial pressure, renal blood flow and heart rate in conscious dogs of a one-hour infusion of atriopeptin 24 (5 $\mu$g/kg) administered alone (as indicated by circles) and after blocking with an $\alpha_1$-adrenergic blocking agent (as indicated by triangles).
Figure 2:
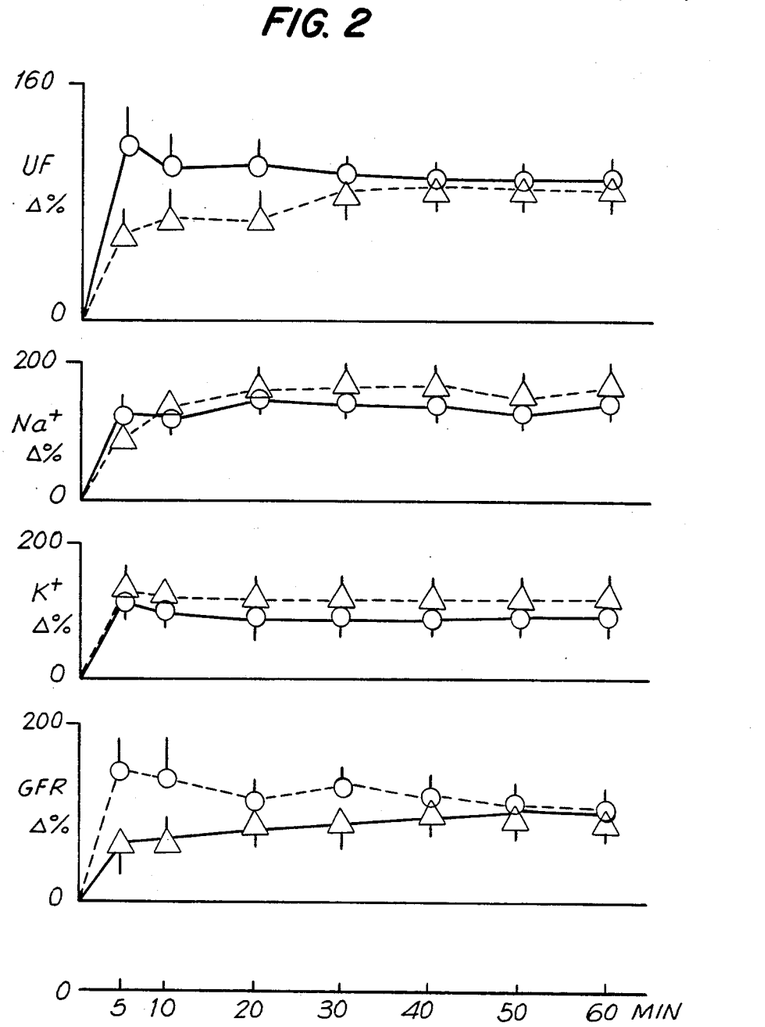
FIG. 2 depicts in graph form the effects on urine flow, sodium and potassium excretion and glomerular filtration rate in conscious dogs of a one-hour infusion of atriopeptin 24 (5 $\mu$g/kg) alone (as indicated by circles) and after blocking with an $\alpha_1$-adrenergic blocking agent (as indicated by triangles).

Infusion of atriopeptin 24 caused an initial transient increase in renal blood flow of 13±2.7% and a decrease in renal vascular resistance of 27±6.1%. The effects, however, returned to control at approximately 30 min (see FIG. 1). Urine flow rate, glomerular filtration rate, and Na and K excretion increased by 104±6.8%, 119±15%, 144±26% and 114±26%, and 114±26%, respectively, and remained elevated at 30 min (see FIG. 2). Hematocrit increased whereas plasma Na (145±1.5 meq/l) and K (3.75±1.3 meq/l) did not change.

At least one week after this infusion, I administered the $\alpha_1$-adrenergic blocking agent, prazosin, at 1 mg/kg to the same five dogs 40 minutes prior to another one-hour infusion of atriopeptin 24 as described above. $\alpha_1$-receptor blockade was assured by the absence of response to phenylephrine (10 $\mu$g/kg).

The prazosin treatment prior to atriopeptin infusion caused a sustained renal vasodilation. At 30 min, renal blood flow was increased by approximately 13% and remained elevated for the duration of the atriopeptin infusion (see FIG. 1). The increase in urine flow rate and glomerular flow rate developed more slowly but increased to the same degree in the presence of the $\alpha_1$-blocking agent as in its absence. Thus, at 30 min, the urine flow rate, glomerular filtration rate and Na and K excretion had increased by 96±21%, 109±19%, 145±5% and 71±6.7%, respectively (see FIG. 2). The effects of the one-hour infusion of atriopeptin 24 on renal hemodynamics and function before and after $\alpha_1$-adrenergic receptor blockade are summarized in the table shown in FIG. 3.

EXAMPLE 2

This example demonstrates the effects of atriopeptin 24 and atriopeptin 28 on renal function in the conscious non-human primate. The data set forth below demonstrate that atriopeptin 24 is more than 4–5 fold as active in the monkey as in the dog.

In this example, I infused conscious monkeys with atriopeptin 24 at 10 $\mu$g/kg/min for 4 min. I also infused conscious monkeys with atriopeptin 28 at a rate of 10 $\mu$g/kg/min for 4 min and one hour later, readministered atriopeptin 24 at 10 $\mu$g/kg/min for 4 min in order to compare the renal effects of atriopeptins 24 and 28 in the same monkeys. In addition, I infused conscious monkeys with atriopeptin 24 at 10 $\mu$g/kg/min for 2 h to determine the renal effects of prolonged infusion of atriopeptin 24. Finally, I compared the effects of infusion of atriopeptin 24 at 10 $\mu$g/kg/min for 4 min in conscious dogs and monkeys.

The experiments were conducted as follows: female monkeys, *Macaca fascicularis*, were anesthetized with ketamine and a Tygon catheter was placed in the femoral artery using sterile surgical techniques. The animals were allowed to recover fully. On each experimental day, the monkeys were sedated with ketamine and the arterial catheter was exteriorized at the back of the neck after infiltrating the area with lidocaine. The Tygon catheter was flushed with saline and attached to a strain gauge manometer (P231D, Statham Instruments Inc.) for the measurement of arterial pressure. An intravenous catheter was placed percutaneously in the leg and the urinary bladder was catheterized using a pediatric Foley catheter (8f). These recording techniques were described in T. H. Hintze et al., "Atriopeptins: Renal-Specific Vasodilators In Conscious Dogs", Am. J. Physiol., 248, pp. H587–91 (1985).

The animals were placed in a primate restraining device and an infusion of saline begun at a rate of 0.1 ml/min for the duration of the experiments. At least 20-min urine collection were taken prior to the administration of the atriopeptins. The atriopeptins were then infused at a rate of 10 $\mu$g/kg/min for 4 min and two 5-min urine collections, then one 10-min collection followed by two 20-min collections were made for determination of effects on urine flow rate and Na and K excretion. Blood samples for the measurement of plasma Na and K and hematocrit were taken twice before the injection of the peptides and during the second 5-min collection period and the first 20-min collection period after infusion of the peptides.

In those experiments in which the effects of atriopeptins 24 and 28 were compared in the same monkey on the same day, the second atriopeptin (i.e., 24) was administered at least one hour after the first. Urine samples were collected as described above. At the end of the day, the monkeys were again sedated with ketamine, the venous and bladder catheters removed and the Tygon catheter buried in the back. The animals were given antibiotics after the initial surgery, at the end of each experiment and when needed if they showed any sign of infection. Each monkey was given at least 10 days to recover before another experiment was performed.

In those experiments in which the effects of a 2-hour atriopeptin 24 infusion were studied, one 5-min urine collection period was followed by ten 10-min collection periods. In addition, inulin was infused to measure glomerular flow rate as described in Example 1.

Using the same techniques in 8 female conscious dogs, the effects of intravenous atriopeptin 24 were examined on urine flow rate, Na and K excretion for comparison. Statistical analysis was performed using a one way analysis for differences from control and a two-way analysis of variance for differences between groups as described in Example 1 above.

Infusion of atriopeptin 24 at 10 μg/kg/min for 4 min resulted in a maximum fall in mean arterial pressure of 9.5±1.4% from 110±5.0 mmHg and no increase in heart rate (3.0±1.0%) from 161±12 b/min. The effects of atriopeptin 24 on renal function were far more dramatic. Atriopeptin 24 increased urine flow rate 1777±312%, Na excretion 29340±7991% and K excretion 714±154%. Hematocrit, plasma Na and K did not change following the infusion of atriopeptin 24. The effects of this atriopeptin 24 infusion lasted only 25 minutes.

Figure 4:
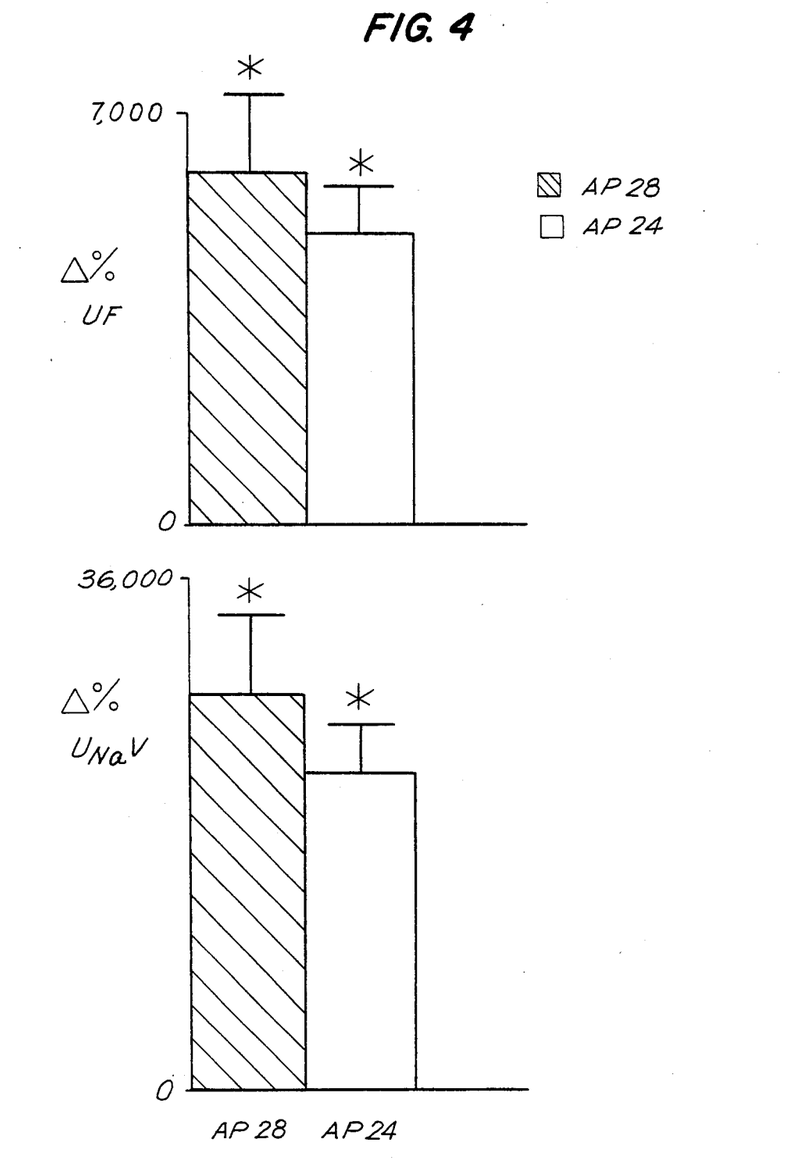
FIG. 4 compares the effects on urine flow rate and sodium excretion of atriopeptin 24 (open bars) and atriopeptin 28 (striped bars) at 10 $\mu$g/kg/min for 4 min in conscious monkeys.

Atriopeptin 28 had even greater effects on renal function than did atriopeptin 24. Atriopeptin 28 increased urine flow rate 5912±1351% and increased Na and K excretion 27839±5592% and 2036±550%, respectively. A comparison of the effects of atriopeptins 24 and 28 in the same monkeys is shown in FIG. 4. Hematocrit, plasma Na and K following the infusion of atriopeptin 28 did not change. The effects of this atriopeptin 28 infusion lasted 30 minutes.

Figure 5:
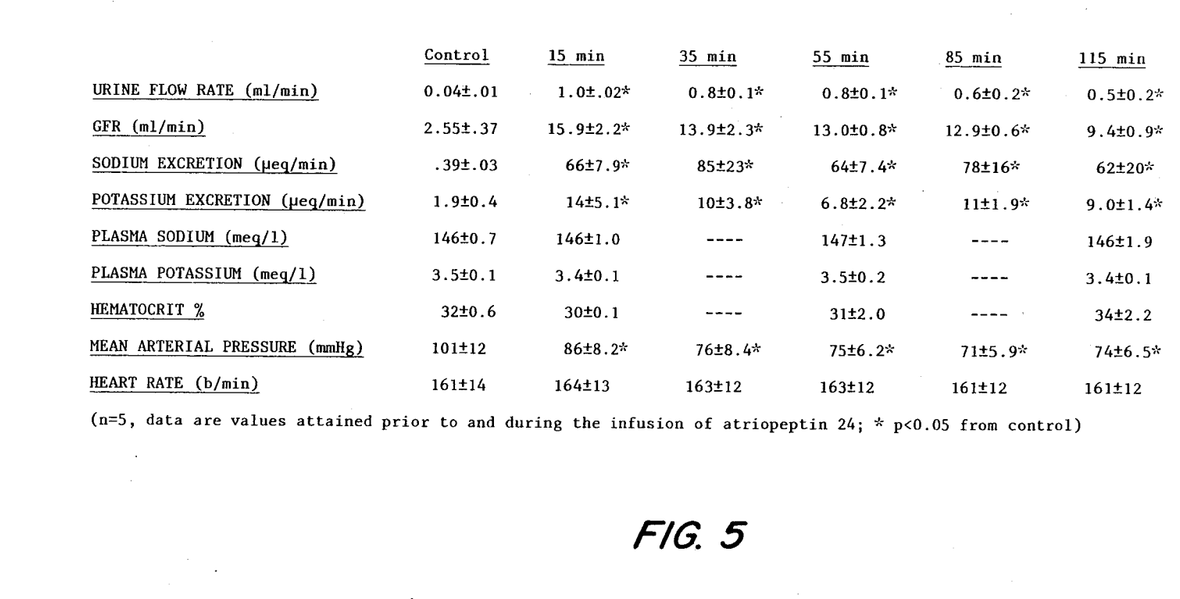
FIG. 5 depicts in table form the effects of a 2-hour infusion of atriopeptin 24 at 10 $\mu$g/kg/min in conscious monkeys.

The effects of a prolonged 2-hour infusion of atriopeptin 24 on renal function are shown in FIG. 5. The magnitude of the initial response to the infusion of atriopeptin 24 was similar to the effects of acute infusion. After the initial striking diuresis, urine flow rate fell but remained elevated more than 12-fold for the duration of the experiments. The excretion of Na and K was also elevated for the duration of the infusion of atriopeptin 24. Surprisingly, the hematocrit did not fall during the infusion of atriopeptin 24 for 2 hours. In these monkeys, glomerular filtration rate increased by more than 200% during the infusion of atriopeptin 24.

Figure 6:
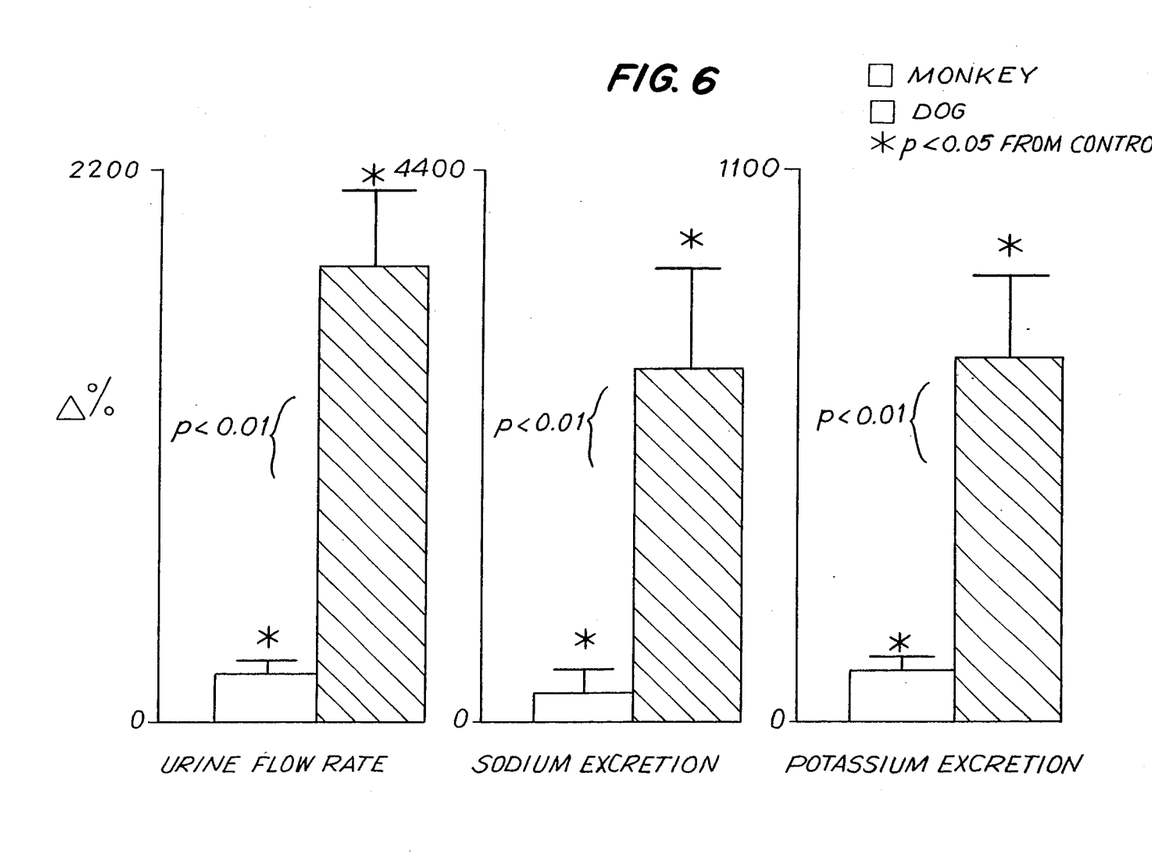
FIG. 6 compares the effects on urine flow rate and sodium and potassium excretion of atriopeptin 24 at 10 $\mu$g/kg/min for 4 min in conscious dogs and monkeys.

Finally, a comparison of the effects of atriopeptin 24 on urine flow rate, Na and K excretion at 10 μg/kg/min for 4 min in the conscious dog and monkey are shown in FIG. 6. The dog showed less dramatic effects of the atriopeptin 24 infusion on renal function than did the monkey. In the dog, however, atriopeptin 24 reduced mean arterial pressure by 12±3.0% and increased heart rate by 15±2.0%.

While I have hereinbefore presented a number of embodiments of this invention, it is apparent that the basic construction can be altered to provide other embodiments which utilize the combinations and methods of this invention. Therefore, it will be appreciated that the scope of this invention is to be defined by the claims appended hereto rather than by the specific embodiments which have been presented hereinbefore by way of example.

I claim:

1. A combination of an atriopeptin having renal vasodilator activity and a compound selected from the group consisting of $\alpha_1$-adrenergic blocking agents and ganglionic blocking agents.

2. The combination according to claim 1, comprising an atriopeptin having renal vasodilator activity and an $\alpha_1$-adrenergic blocking agent.

3. The combination according to claim 1, wherein the atriopeptin is selected from the group consisting of atriopeptin 23, atriopeptin 24 and atriopeptin 28.

4. The combination according to claim 1, wherein the atriopeptin is selected from the group consisting of natural atriopeptins, synthetic atriopeptins, recombinant atriopeptins and derivatives thereof that display renal vasodilator activity.

5. The combination according to claim 1, wherein the $\alpha_1$-adrenergic blocking agent is selected from the group consisting of prazosin and its derivatives such as trimazosin, the haloalkylamines such as phenoxybenzamine and dibenamine, phentolamine, tolazoiline, azapetine, chlorpromazine, haloeridol, the benzodioxans, and the ergot alkaloids.

6. The combination according to claim 5, wherein the ratio of the $\alpha_1$-adrenergic blocking agent to atriopeptin is between about 0.1 mg and 1 mg blocking agent per between about 0.1 μg and 100 μg atriopeptin.

7. The combination according to claim 1, wherein the ganglionic blocking agent is selected from the group consisting of hexamethonium, pentolinium, chlorisondamine, trimethidinium, trimethaphan, mecamylamine, and pempidine.

8. The combination according to claim 7, wherein the ratio of the ganglionic blocking agent to atriopeptin is between about 0.1 mg and 10 mg blocking agent per between about 0.1 mg and 10 mg blocking agent per between about 0.1 μg and 100 μg atriopeptin.

9. A method for treating renal disease or cardiovascular disease or hypertension in mammals comprising the step of administering to the mammal a pharmaceutically effective amount of an atriopeptin having renal vasodilator activity and a pharmaceutically effective amount of a compound selected from the group consisting of $\alpha_1$-adrenergic blocking agents and ganglionic blocking agents.

10. A method for treating renal disease or cardiovascular disease or hyperension in mammals comprising the step of administering to the mammal a pharmaceutically effective amount of an atropeptin having renal vasodilator activity and a pharmaceutically effective amount of an $\alpha_1$-adrenergic blocking agent.

11. The method of claim 9, wherein the atriopeptin is selected from the group consisting of atriopeptin 23, atripeptin 24 and atriopeptin 28.

12. The method of claim 9, wherein the atriopeptin is selected from the group consisting of natural atriopeptins, synthetic atriopeptins, recombinant atriopeptins and derivatives thereof having renal vasodilator activity.

13. The method of claim 9, wherein the atriopeptin is administered at a dosage of between about 0.1 μg/kg and 100 μg/kg body weight.

14. The method of claim 9, wherein the atriopeptin is administered at a dosage of between about 0.1 μg/kg and 10 μg/kg body weight.

15. The method of claim 9, wherein the $\alpha_1$-adrenergic blocking agent is selected from the group consisting of prazosin and its derivatives such as trimazosin, the haloalkylamines such as phenoxybenzamine and dibenamine, phentolamine, tolazoline, azepetine, chlorpromazine, haloperidol, the benzodioxans, and the ergot alkaloids.

16. The method of claim 15, wherein the $\alpha_1$-adrenergic blocking agent is administered at a dosage of between about 0.1 mg/kg and 1 mg/kg body weight.

17. The method of claim 9, wherein the ganglionic blocking agent is selected from the group consisting of hexamethonium, pentolinium, chlorisondamine, trimethidinium, trimethaphan, mecamylamine, and pempidine.

18. The method of claim 17, wherein the ganglionic blocking agent is administered at a dosage of between about 0.1 mg/kg and 10 mg/kg body weight.

19. The method according to claim 9, wherein the mammal is a human.

20. The method according to claim 9, wherein the $\alpha_1$-adrenergic blocking agent or ganglionic blocking agent is administered prior to the renal vasodilator.

* * * * *